United States Patent
Andoh et al.

(10) Patent No.: US 10,295,591 B2
(45) Date of Patent: May 21, 2019

(54) METHOD AND DEVICE FOR TESTING WAFERS

(71) Applicant: Texas Instruments Incorporated, Dallas, TX (US)

(72) Inventors: Takeki Andoh, Tsukuba (JP); Hiroshi Kubota, Itako (JP)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 277 days.

(21) Appl. No.: 13/732,782

(22) Filed: Jan. 2, 2013

(65) Prior Publication Data

US 2014/0184259 A1  Jul. 3, 2014

(51) Int. Cl.
*G01R 31/20* (2006.01)
*G01R 31/28* (2006.01)
*H01L 21/00* (2006.01)
*C12Q 1/00* (2006.01)
*H05K 1/00* (2006.01)
*G01R 1/00* (2006.01)

(52) U.S. Cl.
CPC ..... *G01R 31/2881* (2013.01); *G01R 31/2886* (2013.01); *C12Q 1/00* (2013.01); *C12Q 2304/00* (2013.01); *G01R 1/00* (2013.01); *H01L 21/00* (2013.01); *H01L 2221/00* (2013.01); *H05K 1/00* (2013.01)

(58) Field of Classification Search
CPC ....... H01L 21/00; H01L 2221/00; G01R 1/00; H05K 1/00; H05K 2201/00; H05K 999/00; C12Q 1/00; C12Q 2304/00
USPC .................................................. 324/754.07
See application file for complete search history.

(56) References Cited

U.S. PATENT DOCUMENTS

| | | | |
|---|---|---|---|
| 3,944,447 A * | 3/1976 | Magdo et al. ................ 438/408 |
| 5,410,162 A * | 4/1995 | Tigelaar ............ G01R 31/2831 148/DIG. 162 |
| 6,288,561 B1 * | 9/2001 | Leedy ...................... 324/750.07 |
| 6,414,477 B1 * | 7/2002 | Strom ........................... 702/104 |
| 6,894,308 B2 * | 5/2005 | Whetsel .......... G01R 31/318541 257/48 |
| 2002/0022435 A1 * | 2/2002 | DePalma ................... B24C 9/00 451/2 |
| 2004/0183561 A1 * | 9/2004 | Takekoshi et al. ........... 324/765 |
| 2004/0187452 A1 * | 9/2004 | Edo ................... H01L 21/67017 55/385.2 |
| 2005/0167783 A1 * | 8/2005 | Fujimoto ........... G01R 31/2856 257/536 |
| 2005/0237071 A1 * | 10/2005 | Ito ...................... G01R 31/2886 324/757.01 |
| 2006/0201232 A1 * | 9/2006 | Itakura ................. G01N 27/223 73/1.02 |
| 2008/0084772 A1 * | 4/2008 | Won ....................... G11C 5/145 365/201 |

(Continued)

*Primary Examiner* — Jermele M Hollington
*Assistant Examiner* — Temilades S Rhodes-Vivour
(74) *Attorney, Agent, or Firm* — Ronald O. Neerings; Charles A. Brill; Frank D. Cimino

(57) ABSTRACT

Circuits and methods for testing wafers are disclosed herein. An embodiment of a method includes electrically contacting a first probe and a second probe to a wafer. A gas is blown in the areas proximate the first probe and the second probe. An electric potential is then applied between the first probe and the second probe while the gas is being blown.

17 Claims, 2 Drawing Sheets

(56) References Cited

U.S. PATENT DOCUMENTS

| | | | |
|---|---|---|---|
| 2008/0093340 A1* | 4/2008 | Nakamori | H01L 21/02019 216/57 |
| 2008/0290882 A1* | 11/2008 | Rogers | G01R 1/36 324/755.11 |
| 2009/0058438 A1* | 3/2009 | Ku | G01R 31/2851 324/750.3 |
| 2009/0191340 A1* | 7/2009 | Tozawa | H01L 21/02063 427/255.39 |
| 2010/0058606 A1* | 3/2010 | Nakashima | B01B 1/005 34/218 |
| 2010/0201391 A1* | 8/2010 | Gunji | G01R 31/2875 324/750.03 |
| 2011/0115514 A1* | 5/2011 | Komatsu | 324/754.14 |
| 2011/0259521 A1* | 10/2011 | Hyakutake | B01D 53/185 156/345.29 |
| 2013/0077651 A1* | 3/2013 | Lee | H01L 21/67253 374/28 |
| 2013/0141127 A1* | 6/2013 | Yasuta | G01R 1/067 324/750.03 |
| 2014/0184259 A1* | 7/2014 | Andoh | G01R 31/2886 324/754.07 |

* cited by examiner

METHOD AND DEVICE FOR TESTING WAFERS

BACKGROUND

Some integrated circuits are required to undergo high voltage testing prior to packaging. In many situations, the testing is performed at the wafer level in order to identify defective integrated circuits on the wafer before they are processed into individual packages. The testing may involve the use of a wafer prober that includes a first probe and a second probe. The probes contact specific portions of the wafer and then apply a voltage potential between the first probe and the second probe.

Integrated circuits located on the wafer are very small, so the first probe and the second probe are typically very close to each other. The close proximity of the first probe to the second probe may cause problems during the high voltage tests, and even low voltage tests. For example, humidity or condensation on the wafer or the wafer probes may cause a slight current flow between the first probe and the second probe, which is referred to as leakage. The leakage reduces the voltage potential between the first probe and the second probe, so the integrated circuits on the wafer are not subjected to the intended high voltage.

Currently, high voltage testing of wafers is conducted in an environmentally controlled chamber in the wafer prober. The wafer is placed in the chamber and electrically connected to a test card. The chamber is filled with a gas, such as nitrogen, to dry the wafer and the test card. After a period, which is commonly as long as twenty minutes, the wafer and the test card are assumed to be dry and the wafer is tested. This procedure is very time consuming.

SUMMARY

Circuits and methods for testing wafers are disclosed herein. An embodiment of a method includes electrically contacting a first probe and a second probe to a wafer. A gas is blown in the areas proximate the first probe and the second probe. An electric potential is then applied between the first probe and the second probe while the gas is being blown.

DETAILED DESCRIPTION

Test stations and methods of testing wafers are disclosed herein. The test stations are sometimes referred to as wafer probers. The test stations and testing methods apply a voltage, which may be a relatively high voltage to the wafers. In conventional testing methods and test stations, the wafers are placed in a chamber that is filled with nitrogen or another gas in order to provide dry ambient conditions during the voltage testing, which reduces leakage during the testing. The test stations and methods disclosed herein overcome the long testing cycle involved in filling a chamber with a gas by blowing the gas onto the wafer and high voltage components of the test station without the use of a gas-filled chamber.

Figure 1:
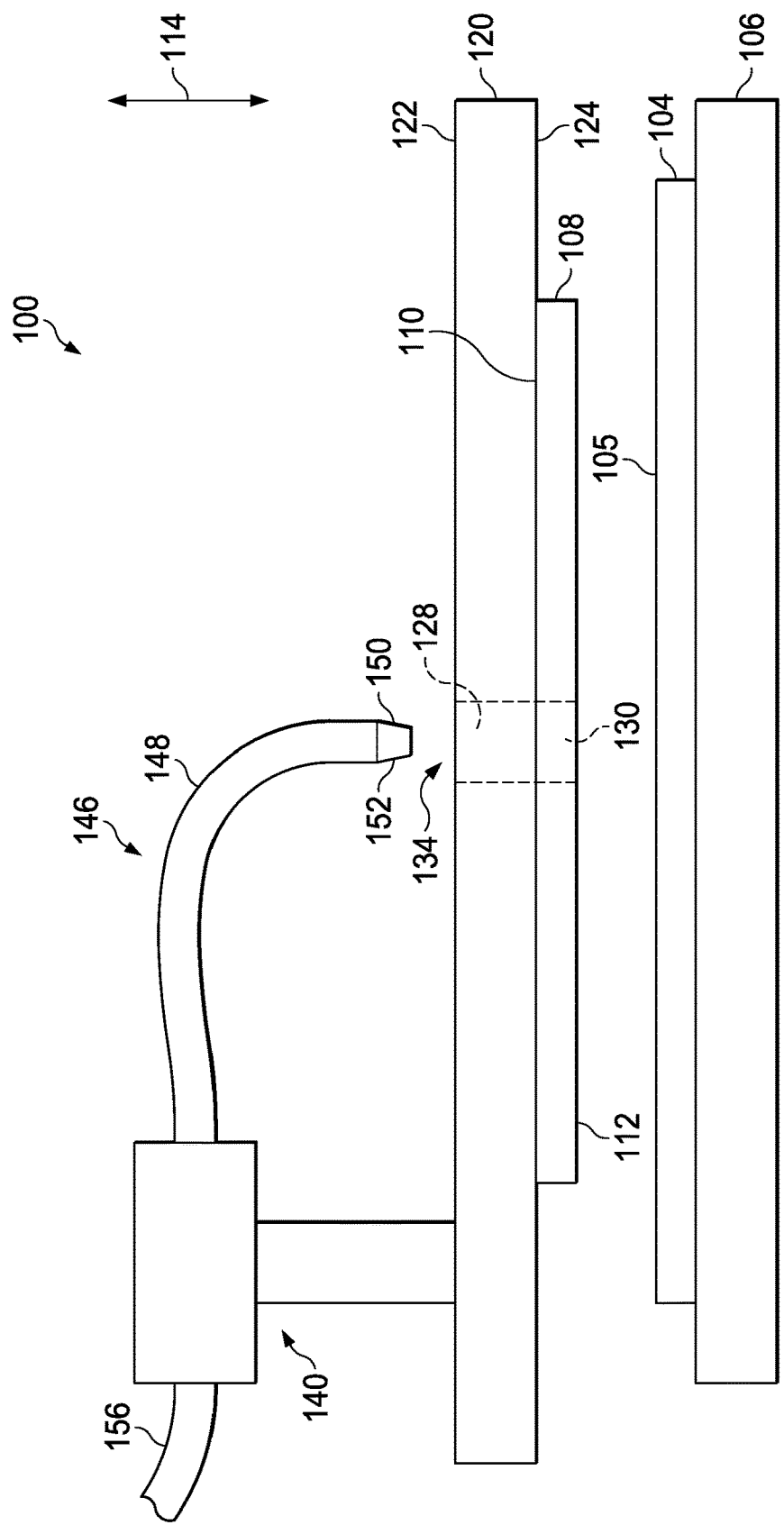
FIG. 1 is a side elevation view of an embodiment of a portion of a wafer prober.

A side elevation view of the interior of a test station 100 is shown in FIG. 1. It is noted that the test station 100 shown in FIG. 1 is a partial view of a type of test station often referred to as a wafer prober, but includes the applicants' modifications. The test station 100 may include other components that are well-known in the art, but are not shown or described herein. The test station 100 is used to test a wafer 104. The wafer 104 has a surface 105 that has a plurality of integrated circuits (not shown in FIG. 1) fabricated onto it. It is noted that devices other than wafers may be tested by the test station 100 and methods described herein.

The wafer 104 is attached to a plate 106 that may be movable within the test station 100. The plate 106 assures that the wafer 104 is located in a precise location within the test station 100 as is known in the art. The test station 100 includes a test card 108 that has an upper side 110 (sometimes referred to as a first side) and an opposite lower side 112 (sometimes referred to as a second side). The test card 108 includes a plurality of probes (not shown in FIG. 1) extending from the lower side 112 that are aligned with conductors on the integrated circuit during testing. The plate 106 is movable in a direction 114 relative to the test card 108, which enables the probes on the test card 108 to contact the integrated circuits on the wafer 104. It is noted that in some embodiments the test card 108 may be movable relative to the plate 106, which may be in a fixed location.

The test station 100 also includes a head 120 having an upper side 122 (sometimes referred to as a first side) and a lower side 124 (sometimes referred to as a second side). The upper side 110 of the test card 108 is attached to the lower side 124 of the head 120. The attachment of the test card 108 to the head 120 further assures that the probes on the test card 108 align with conductors on the integrated circuits during testing.

The head 120 has a hole 128 that is aligned with a hole 130 in the test card 108. The holes 128, 130 provide a single hole 134 extending between the upper side 122 of the head 120 and the lower side 112 of the test card 108. As described below, the hole 134 is configured to enable a gas to be blown through the test card 108 and the head 120 to contact the test card 108 and the surface 105 of the wafer 104.

A hose mount 140 may be attached to the upper side 122 of the head 120 or other device within the test station 100. The hose mount 140 serves to maintain a hose 146 in a fixed position relative to the hole 134. It is noted that other mechanisms may be used to secure the hose 146 within the test station 100. The hose 146 includes a rigid or semi-rigid portion 148 that is attached to the hose mount 140. A nozzle 150 is located at a first end 152 of the hose 146. The hose 146 may have a flexible portion 156 that is connected to a gas supply (not shown). The rigid portion 148 of the hose 146 enables the nozzle 150 to be positioned in a predetermined location relative to the hole 134 so as to enable gas to be blown from the nozzle 150 and through the hole 134. The gas then contacts the wafer 104 and the test card 108. The gas has been described as being deliverable by way of the hose 146. However, it is to be understood that any gas delivery device that blows gas proximate the wafer 104 and/or the test card 108 may be used.

Figure 2:
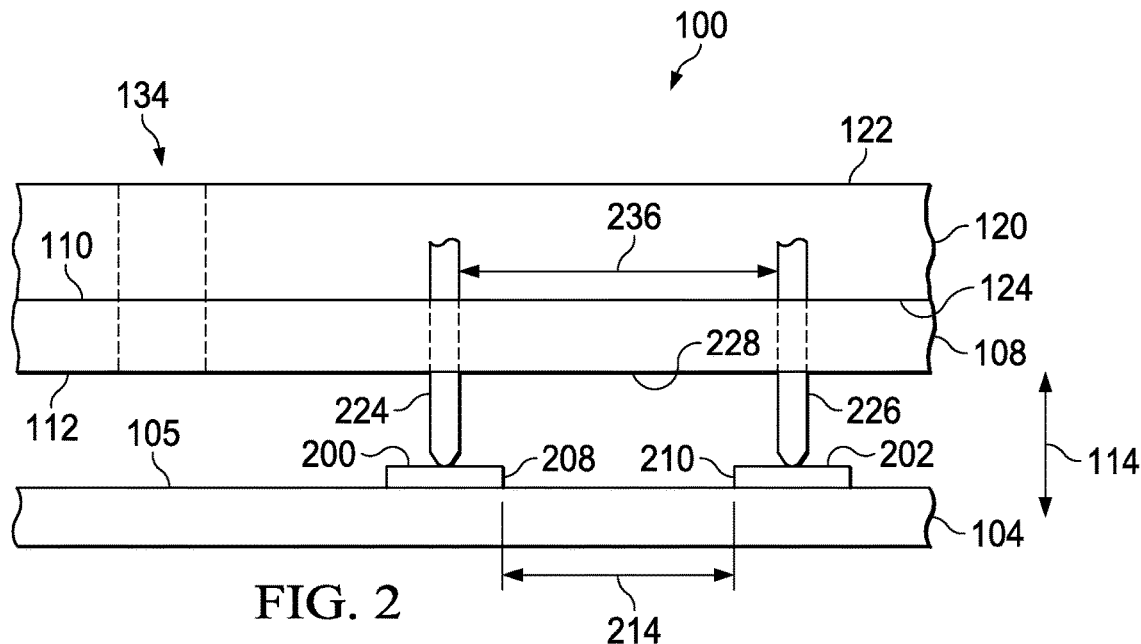
FIG. 2 is an enlarged view of a portion of a wafer and test card used in the wafer prober of FIG. 1.

FIG. 2 is an enlarged view of the wafer 104 and test card 108 of FIG. 1. The enlarged view of FIG. 2 shows components on the wafer 104 and the test card 108 that can cause leakage. The wafer 104 of FIG. 2 shows a portion of an integrated circuit having a first pad 200 and a second pad 202. The pads 200, 202 are locations on the wafer 104 where electrical contacts may be made. For example, the pads 200, 202 may be traces or widened portions of traces. The pads 200, 202 may also be locations on the wafer 104 specifically designed for electrical tests. In the embodiment of FIG. 2, the pads 200, 202 are adapted for high voltage tests. For example, a voltage potential of approximately 1,000 volts may be applied between the pads 200, 202.

The first pad 200 has an edge 208 that faces the second pad 202 and the second pad 202 has an edge 210 that faces the first pad 200. The edges 208, 210 are separated by a distance 214, which may be a few microns. As described in greater detail below, leakage between the first pad 200 and the second pad 202 may occur between the edges 208, 210 due to the very small distance 214 and the high voltage potential between the pads 200, 202.

The test card 108 has a first probe 224 and a second probe 226 extending from the second side 112. As shown in FIG. 2, the probes 224, 226 may pass through the test card 108 so that the portions of the probes 224, 226 extending though the first side 110 are connected to high voltage supplies (not shown). For example, the probes 224, 226 may be connected to wires or traces (not shown) on the test card 108 that are connected to testing devices (not shown) in the test station 100. The first probe 224 is separated from the second probe 226 by a distance 236, which may be a few microns and that may be slightly greater than the distance 214.

As described above, the test card 108 and/or the wafer 104 are movable along the axis 114. In the embodiment described herein, the wafer 104 is moved along the axis 114 toward the test card 108 until the probes 224, 226 contact the pads 200, 202. In some embodiments, the probes 224, 226 are not rigidly affixed to the test card 108, but rather are affixed by way of a spring mechanism (not shown). Therefore, both probes 224, 226 may contact the pads 200, 204 without damaging the pads 200, 202. When the probes 224, 226 contact the pads 200, 204, the high voltage testing may commence. A high voltage potential is applied between the first probe 200 and the second probe 202 in order to test portions and/or parameters of the an integrated circuit fabricated on the wafer 104.

Leakage between the first probe 224 and the second probe 226 may occur during the high voltage tests because of the high voltage potential and the short distance 236 between the probes 224, 226. Likewise, leakage may occur between the pads 200, 204 as describe above. The distance 236 between the probes 224, 226 is greater than the distance 214 between the edges 208, 210 of the pads 200, 202, however, the probes 224, 226 may have much more surface area than the edges 208, 210, so leakage between the probes 224, 226 may be significant relative to leakage between the pads 200, 202.

The leakage reduces the voltage potential between the first probe 224 and the second probe 226. The leakage is dependent on the relative humidity of the ambient air in the proximity of the wafer 104 and the test card 108. For example, if the wafer 104 is tested in a high humidity environment, the leakage will be greater than if the wafer 104 is tested in a dry environment. In conventional test stations, the wafer 104 is placed in a chamber that is filled with a dry gas, such as nitrogen. The dry gas replaces any humid ambient air that may be between the pads 204, 206 and between the probes 224, 226. When the ambient air has been replaced by the gas used by the conventional test station, the high voltage testing commences.

The conventional test stations take a long time to perform a single test. Replacing the ambient air with the gas used by the test station may take as long as twenty minutes.

In order to overcome the problems associated with the gas-filled chamber of conventional test stations, the test station 100 described herein has the hose 146 that blows a gas onto the wafer 104 and the test card 108. The gas blown by the hose 146 provides a dry ambient environment proximate the wafer 104 and the test card 108. Therefore, leakage due to high humid conditions is eliminated. In some embodiments, nitrogen is used as the gas. In other embodiments, ambient air, sometimes referred to as clean, dry air is blow from the hose 146. In order to have a dry air or gas blown from the hose 146, the test station 100 may include a dehumidifier (not shown) or other device that removes moisture from a gas before the gas is blown on the wafer 104. In addition, the test station 100 may include a filter (not shown) that prevents contaminants from being blown by the hose 146.

Figure 3:
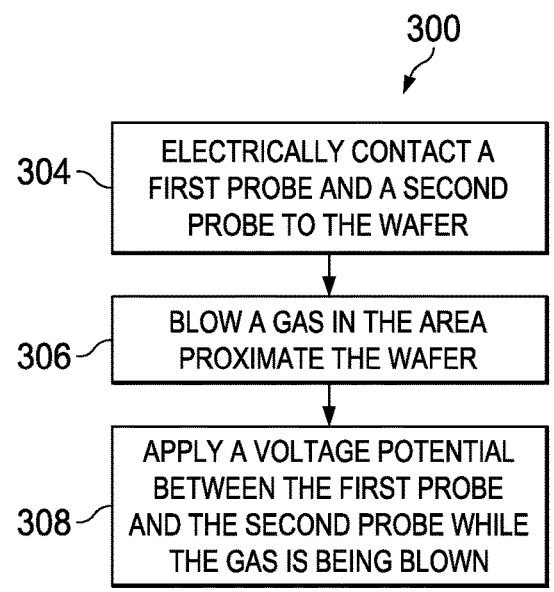
FIG. 3 is a flow chart describing the operation of the wafer prober of FIG. 1.

Having described the test station 100, its operation will now be described with reference to the flow chart 300 of FIG. 3. In step 304, the probes 224, 226 contact the pads 200, 202. For example, the test card 108 may be moved along the axis 114 so that the probes 224, 226 contact the pads 200, 204. In step 306, the gas is blown onto the area proximate the probes 224, 226 and the wafer 104. In step 308, a voltage potential is applied between the first probe 224 and the second probe 226 while the gas is being blown. When the testing is complete, the wafer 104 is removed and the next wafer to be tested is placed into the test station 100. The complete test may only take a few minutes because the testing time is significantly reduced by blowing air onto the wafer 104 and the test card 108 rather than placing the wafer into a chamber and filling the chamber with gas.

The foregoing description of specific embodiments of methods and devices for testing wafers has been presented for purposes of illustration and description. The specific embodiments described are not intended to be exhaustive or to suggest a constraint to the precise forms disclosed, and many modifications and variations are possible in light of the above teaching. The illustrated embodiments were chosen and described in order to best explain principles and practical application, to thereby enable others skilled in the art to best utilize the various embodiments with various modifications as are suited to the particular use contemplated. It is intended that the language of the claims appended hereto be broadly construed so as to cover different embodiments of the structures and methods expressly disclosed here, except as limited by the prior art.

What is claimed is:

1. A method for testing of wafers, the method comprising:
electrically contacting a first probe to a wafer;
electrically contacting a second probe to the wafer;
blowing a gas in an area proximate the first probe and the second probe, the gas being blown through a hole in a test card, the first probe and the second probe being connected to the test card, wherein moisture is removed from the gas before the gas is blown; and
applying an electric potential between the first probe and the second probe while the gas is blown in the area proximate the first and second probe.

2. The method of claim 1, wherein the gas is nitrogen.

3. The method of claim 1, wherein the gas is air.

4. The method of claim 1, wherein the wafer has conductive pads located thereon and wherein the electrically contacting comprises contacting the first probe and the second probe to the conductive pads.

5. A method for testing of wafers, the method comprising:
electrically contacting a first probe to a wafer;
electrically contacting a second probe to the wafer;
blowing a gas in an area proximate the first probe and the second probe, the gas being blown through a hole in a test card, the first probe and the second probe being connected to the test card, wherein moisture is removed from the gas before the gas is blown; and applying approximately is one thousand volts between the first probe and the second probe while the gas is blown in the area proximate the first and second probe.

6. A device for testing a wafer, the device comprising:
a first probe that is electrically connectable to the wafer;
a second probe that is electrically connectable to the wafer, wherein the first probe and the second probe are connected to a test card having a hole located therein and wherein an electric potential is able to be developed between the first probe and the second probe;
a gas delivery device that delivers gas to an area proximate the first probe and the second probe when the electric potential is being developed between the first probe and the second probe, the gas delivery device delivers the gas through the hole of the test card; and
a dehumidifier for removing moisture from the gas before the gas is delivered.

7. The device of claim 6, wherein the gas is nitrogen.
8. The device of claim 6, wherein the gas is air.
9. The device of claim 6, wherein the gas delivery device is a hose.

10. A device for testing a wafer, the device comprising:
a first probe that is electrically connectable to the wafer;
a second probe that is electrically connectable to the wafer, wherein the first probe and the second probe are connected to a test card having a hole located therein and wherein an electric potential is able to be developed between the first probe and the second probe;
a gas delivery device that delivers gas to an area proximate the first probe and the second probe when the electric potential is being developed between the first probe and the second probe, the gas delivery device delivers the gas through the hole of the test card; and
a dehumidifier for removing moisture from the as before the as is delivered, wherein the gas delivery device is a hose having an end, wherein the gas is emitted at the end of the hose, and wherein the end of the hose is located proximate the hole.

11. A device for testing a wafer, the device comprising:
a first probe that is electrically connectable to the wafer;
a second probe that is electrically connectable to the wafer, wherein the first probe and the second probe are connected to a test card having a hole located therein and wherein an electric potential is able to be developed between the first probe and the second probe;
a gas delivery device that delivers gas to an area proximate the first probe and the second probe when the electric potential is being developed between the first probe and the second probe, the gas delivery device delivers the gas through the hole of the test card;
a dehumidifier for removing moisture from the gas before the gas is delivered; and
a test head, wherein the test card is connected to the test head, the test head having a hole aligned with the hole in the test card.

12. The device of claim 11, wherein the gas delivery device is a hose having an end, wherein the gas is emitted at the end of the hose, and wherein the end of the hose is located proximate the hole in the test head.

13. A device for testing a wafer, the device comprising:
a first probe that is electrically connectable to the wafer;
a second probe that is electrically connectable to the wafer, wherein the first probe and the second probe are connected to a test card having a hole located therein and wherein an electric potential is able to be developed between the first probe and the second probe;
a as delivery device that delivers gas to an area proximate the first probe and the second probe when the electric potential is being developed between the first probe and the second probe, the gas delivery device delivers the as through the hole of the test card, wherein the test card is movable within the device and wherein the gas delivery device is movable with the test card; and
a dehumidifier for removing moisture from the gas before the gas is delivered.

14. A method for testing wafers, the method comprising:
providing a test card with a hole, the test circuit having a first probe and a second probe;
blowing a gas in an area proximate the first probe, the second probe, and the wafer, the gas being blown through the hole in the test card, wherein moisture is removed from the gas before the gas is blown;
electrically contacting the first probe to the wafer;
electrically contacting the second probe to the wafer; and
applying an electric potential between the first probe and the second probe while the gas is blown.

15. The method of claim 14, wherein the gas is air.
16. The method of claim 14, wherein the gas is nitrogen.
17. The method of claim 14 further comprising: moving the test card proximate the wafer.

* * * * *